US008307722B2

(12) United States Patent
Tajima et al.

(10) Patent No.: US 8,307,722 B2
(45) Date of Patent: Nov. 13, 2012

(54) METHOD OF DETECTING DISPENSED QUANTITY, AND LIQUID SUCTION MONITORING DISPENSING APPARATUS

(75) Inventors: Hideji Tajima, Chiba (JP); Michinori Koizuka, Chiba (JP); Hiroshi Suzuki, Chiba (JP); Susumu Kimura, Chiba (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 850 days.

(21) Appl. No.: 11/920,663

(22) PCT Filed: May 19, 2006

(86) PCT No.: PCT/JP2006/310004
§ 371 (c)(1),
(2), (4) Date: Feb. 20, 2009

(87) PCT Pub. No.: WO2006/123771
PCT Pub. Date: Nov. 23, 2006

(65) Prior Publication Data
US 2009/0211380 A1    Aug. 27, 2009

(30) Foreign Application Priority Data

May 19, 2005  (JP) .................................. 2005-147108

(51) Int. Cl.
*G01N 1/14*        (2006.01)
(52) U.S. Cl. .................... 73/864.11; 73/1.74; 73/864.34
(58) Field of Classification Search .................... 73/1.74, 73/864.34, 864.11
See application file for complete search history.

(56) References Cited

U.S. PATENT DOCUMENTS 4,780,833 A * 10/1988 Atake ........................ 73/864.14
(Continued)

FOREIGN PATENT DOCUMENTS
JP           62-64912           3/1987
(Continued)

OTHER PUBLICATIONS

International Search Report, issued by the Japanese Patent Office, mailed Aug. 22, 2006, in connection with International Application No. PCT/JP2006/310004.

(Continued)

*Primary Examiner* — Hezron E Williams
*Assistant Examiner* — Nashmiya Fayyaz
(74) *Attorney, Agent, or Firm* — Haynes and Boone, LLP

(57) ABSTRACT

There are provided a method of detecting dispensed quantity in which without the need of detecting a surface of liquid accommodated in a container, a liquid quantity can be detected only by measuring pressure change; and a relevant liquid suction monitoring dispensing apparatus. There is provided a method of detecting dispensed quantity for detection of the quantity of liquid suctioned and discharged by a dispensing apparatus including a pipette tip, a liquid suctioning/discharging mechanism for the pipette tip, a pressure sensor capable of detecting the pressure within the pipette tip, and a lifting and lowering mechanism for the pipette tip, which method comprises: an insertion step for inserting a distal end of the pipette tip down to the deepest zone of a container accommodating liquid to be measured; a suction pressure measuring step for without moving of the pipette tip, while suctioning the liquid into the pipette tip at a predetermined suctioning rate, measuring any pressure change during the suctioning; and a suction detecting step for on the basis of pressure change measured, determining the state of suction. Further, there is provided a liquid suction monitoring dispensing apparatus capable of practicing this method.

14 Claims, 9 Drawing Sheets

U.S. PATENT DOCUMENTS

| | | | |
|---|---|---|---|
| 5,499,545 | A | 3/1996 | Kimura et al. |
| 5,503,036 | A * | 4/1996 | Nguyen et al. ............. 73/864.34 |
| 5,537,880 | A * | 7/1996 | Takeda et al. ............. 73/864.25 |
| 5,965,828 | A | 10/1999 | Merriam |
| 6,121,049 | A | 9/2000 | Dorenkott et al. |
| 6,203,759 | B1 | 3/2001 | Pelc et al. |
| 6,370,942 | B1 | 4/2002 | Dunfee et al. |
| 6,521,187 | B1 | 2/2003 | Papen |
| 2004/0149015 | A1 * | 8/2004 | Hansen et al. ................... 73/40 |

FOREIGN PATENT DOCUMENTS

| | | |
|---|---|---|
| JP | 9-257805 | 10/1997 |
| JP | 11-94844 | 4/1999 |
| JP | 2003-149093 | 5/2003 |
| JP | 2004-245715 | 9/2004 |
| JP | 2005-37157 | 2/2005 |

OTHER PUBLICATIONS

Written Opinion, issued by the Japanese Patent Office, mailed Aug. 22, 2006, in connection with International Application No. PCT/JP2006/310004.

International Preliminary Report on Patentability, issued by the Japanese Patent Office, mailed Sep. 11, 2007, in connection with International Application No. PCT/JP2006/310004.

Supplementary European Search Report for International Application No. EP06756360 dated Jul. 28, 2011.

* cited by examiner

METHOD OF DETECTING DISPENSED QUANTITY, AND LIQUID SUCTION MONITORING DISPENSING APPARATUS

CROSS REFERENCE

This application is a United States national phase application of co-pending international patent application number PCT/JP2006/310004, filed May 19, 2006, which claims priority to Japanese patent application number 2005-147108, filed May 19, 2005, the disclosures of which are incorporated herein by reference.

TECHNICAL FIELD

The present invention relates to a method of detecting dispensed quantity which uses changes in air pressure to detect a suction quantity of liquid, and a liquid quantity monitoring dispensing apparatus, in particular, to a method of monitoring liquid quantity detection based on changes in suction pressure in a dispensing apparatus that suctions liquid suspended with biological material into a pipette tip and dispenses the liquid into an examination container, and to an apparatus that employs this method.

BACKGROUND ART

Conventionally, there has been a dispensing method in which a suction quantity is detected and evaluated by suctioning liquid from a container into a pipette tip with a dispensing apparatus (Patent Document 1). In this dispensing method, (a) when the lower end of a measuring instrument is immersed into liquid to be suctioned by a relative vertical movement between the measuring instrument and a container accommodating the liquid to be suctioned, suction of the liquid is commenced at a point where the pressure fluctuation range after the immersion is at a predetermined value with respect to the inner pressure of the measuring instrument before the lower end of the measuring instrument comes in contact with the liquid to be suctioned, and (b) after a predetermined period of time has elapsed, the lower end of the measuring instrument is separated from the liquid to be suctioned, and at this point it is determined whether or not it is a normal dispensed quantity based on the inner pressure of the measuring instrument.

In addition, there has been a method of pipetting a sample in which a liquid sample is suctioned and the suction state is evaluated, by means of the following method (Patent Document 2).

(a) The pressure inside a pipetter is measured in the initial state, and this value is taken as a reference pressure reading value.

(b) Then while lowering the pipetter towards the liquid sample within a container, the pressure inside the pipetter is made negative to thereby suction air, (c) and in the case of monitoring pressure change within the pipetter, when a rapid pressure change is seen, this is considered to be when the distal end of the pipette tip reaches the liquid surface. Therefore it is considered that the liquid surface has been reached, and lowering of the pipetter and suction are stopped so that the distal end of the pipette tip is positioned within a predetermined distance from the liquid surface.

(d) Next, the pipetter is lowered to further move the distal end of the pipette tip downward (within the range of a prescribed distance), and the accommodated liquid is suctioned from the container into the pipette tip while suctioning the liquid at a volume flow rate that corresponds to the suction pressure (with a controlled suction quantity), (e) changes in the suction pressure are monitored while monitoring this liquid, (f) the measured pressure change is compared with a pre-decided normal suction pressure scheme, and (g) in the case where the pressure value deviates from the normal suction pressure scheme, it is determined that the liquid is heterogeneous or the suction quantity is out of the prescribed quantity.

Patent Document 1: Japanese Unexamined Patent Publication No. 62-64912

Patent Document 2: Japanese Patent Publication No. 3065100

PROBLEMS OF THE PRIOR ART

In a conventional apparatus, the surface of liquid accommodated in a container needs to be detected first, therefore:

(1) The liquid that was suctioned during liquid surface detection needs to be removed from the inside of the pipette tip.

(2) Since the lower end of the pipette tip needs to be lowered so as to conform to the liquid surface while suctioning air, the suctioning step and the lifting and lowering step need to be controlled simultaneously.

(3) In order to carry out the step of detecting the liquid surface first, even if the liquid is not accommodated within the container, lowering of the pipette tip and air suction need to be continued for a certain period of time. On the other hand, in the case where there is sufficient liquid present, deficiency detection during the suction step cannot be carried out.

(4) Since the conventional apparatus is dependent on the shape of the container, a liquid surface-liquid volume conversion table needs to be prepared for each of the container shapes.

(5) Conversion calculation needs to be performed within the processing time, resulting in a loss of processing time. Moreover, the processing time for the step for removing the liquid after detecting the liquid surface becomes a loss of time.

(6) Having detected the liquid surface, if the attached liquid is suctioned into the pipette tip again, then it can be falsely detected as liquid surface detection, resulting in a malfunction.

(7) In the case where bubbles have occurred on the liquid surface, the bubbles may be detected as a liquid surface, giving a false liquid surface detection, resulting in a malfunction.

(8) Since the liquid cannot be completely removed from the distal end of the pipette tip once the pipette tip has been used, a malfunction may occur in the case of reuse or continuous use of the pipette tip.

As mentioned above, a number of problems are observed.

DISCLOSURE OF THE INVENTION

Problems to be Solved by the Invention

The present invention has been achieved in consideration of the above problems in the conventional technique, and its technical object that has been specifically set in order to solve these problems is to provide a method of detecting dispensed quantity and a liquid suction monitoring dispensing apparatus that do not require detection of the surface of liquid accommodated within a container and that enable liquid quantity detection by only measuring pressure change.

Means for Solving the Problems

The following means for effectively solving the problems are specifically configured and include all particulars required in order to specify a method of detecting dispensed quantity and a liquid suction monitoring dispensing apparatus.

A first means for solving the problems according to the method of detecting dispensed quantity of the present invention is a method of detecting dispensed quantity for detecting a suction state of a specified quantity of liquid that is suctioned and discharged by a dispensing apparatus having: a pipette tip; a liquid suctioning/discharging mechanism for the pipette tip; a pressure sensor that detects a pressure inside the pipette tip; and a lifting and lowering mechanism for the pipette tip, wherein the method comprises: an insertion step for inserting a distal end of the pipette tip into a deepest zone of a container that accommodates the liquid to be measured; a suction pressure measuring step for measuring a pressure change during suctioning, while suctioning the liquid into the pipette tip at a predetermined suctioning rate without moving the pipette tip; and a suction detecting step for detecting the suction state of a specified liquid quantity based on a measured pressure change, a shape of the pipette tip, the predetermined suctioning rate, and a period of suction time. Here, since the suction detection is performed "based on the measured pressure change", then for example by comparing the measured pressure change with a preset threshold value, a change rate (temporal differentiation value) based on the measured pressure change is calculated, thereby detecting the suction state, or the suction state may be detected based on the pressure change wave form or pattern in some cases. The "deepest zone" refers to a position where suction of the liquid accommodated inside the container is possible, and is a position on the bottom of the container or a position in close proximity to the bottom of the container.

A second means for solving the problems according to the above method of detecting dispensed quantity is characterized in that in the suction detecting step, the measured pressure change is compared with a preset threshold value, and the suction state is detected based on a pressure value that deviates from the threshold value.

A third means for solving the problems according to the above method of detecting dispensed quantity is characterized in that in the suction detecting step, the presence or absence of a suction deficiency or an empty suction is detected based on a pressure value that deviates from the threshold value.

A fourth means for solving the problems according to the above method of detecting dispensed quantity is characterized in that in the suction detecting step, the presence or absence of the pipette tip is detected based on the presence or absence of the measured pressure change.

If the pressure change is not present, then the absence of the pipette tip is detected.

A fifth means for solving the problems according to the above method of detecting dispensed quantity is characterized in that in the suction detecting step, an occurrence of clogging is detected if a change rate of the pressure change exceeds a preset value.

A sixth means for solving the problems according to the above method of detecting dispensed quantity is characterized in that in the insertion step, the distal end of the pipette tip stops in a position that is distanced from a bottom of the container with a certain gap.

A seventh means for solving the problems according to the above method of detecting dispensed quantity is characterized in that the pipette tip has a small diameter section on which the distal end is provided, and a large diameter section that continues from the small diameter section and that can be connected to the suctioning/discharging mechanism, and in the insertion step, the small diameter section is inserted into the liquid. Here, examples of the shape of the pipette tip that is suitable for this method of detecting dispensed quantity are pipette tips disclosed in Japanese Design Registration No. 1068693 or No. 1068693—type 1. Moreover, as long as there are provided the small diameter section and the large diameter section, then in the intermediate position between them there may be provided an intermediate diameter section with an intermediate diameter between the diameters of the small diameter section and the large diameter section.

A first means for solving the problems according to the liquid suction monitoring dispensing apparatus of the present invention is characterized in that it is provided with: a pipette tip; a lifting and lowering mechanism for this pipette tip; a liquid suctioning/discharging mechanism for the pipette tip; a pressure sensor that detects a pressure inside the pipette tip; and a control section that: operates the lifting and lowering mechanism so as to insert a distal end of the pipette tip into a deepest zone of the container that accommodates the liquid to be measured; operates the suctioning/discharging mechanism so as to suction the liquid into the pipette tip at a predetermined suctioning rate; receives input of a measurement value from the pressure sensor; and detects a suction state based on a measured pressure change, a shape of the pipette tip, the predetermined suctioning rate, and the period of suction time.

A second means for solving the problems according to the above suction monitoring dispensing apparatus is characterized in that the control section compares the measured pressure change with a preset threshold value, and detects a suction state based on a pressure value that deviates from the threshold value.

A third means for solving the problems according to the above suction monitoring dispensing apparatus is characterized in that the pipette tip has a small diameter section on which the distal end is provided, and a large diameter section that continues from the small diameter section and that can be connected to the suctioning/discharging mechanism.

Effects of the Invention

In the first means for solving the problems according to the method of detecting dispensed quantity of the present invention, the suction state of a specified quantity of liquid can be detected by only measuring pressure change, without detecting the surface of the liquid accommodated in the container.

In the second means for solving the problems according to the above method of detecting dispensed quantity, since the measured pressure change is compared with the preset threshold value and detection is based on a pressure value that deviates from the threshold value, the suction state of a specified quantity of the liquid can be easily detected with a high level of reliability.

In the third means for solving the problems according to above method of detecting dispensed quantity, by making a comparison with a preset threshold value, whether the suctioned liquid quantity is deficient or sufficient, and also whether the liquid inside the container has depleted and the container has become empty can be detected.

In the fourth means for solving the problems according to the above method of detecting dispensed quantity, it can be easily and reliably detected that the pipette tip itself is not attached to a nozzle member, by measuring pressure.

In the fifth means for solving the problems according the above method of detecting dispensed quantity, clogging can be easily and reliably detected by observing the change rate of the pressure change.

In the sixth means for solving the problems according to the above method of detecting dispensed quantity, by having the distal end of the pipette tip positioned with a certain gap from the bottom of the container, the suction state becomes uniform, the reliability of a liquid quantity measurement is improved, and a dispensed quantity can be detected at a high level of accuracy.

In the seventh means for solving the problems according to the above method of detecting dispensed quantity, since the pipette tip having the small diameter section and the large diameter section is used, and the liquid comes into contact only with the small diameter section, an influence of the insertion into the liquid can be minimized, and a minute quantity of liquid and also containers with various kinds of shapes can be handled.

In the first means for solving the problems according to the liquid suction monitoring dispensing apparatus of the present invention, the control section: operates the lifting and lowering mechanism so as to insert the distal end of the pipette tip into the deepest zone of the container that accommodates the liquid to be measured; operates the suctioning/discharging mechanism so as to suction the liquid into the pipette tip; receives input of the pressure inside the pipette tip during the suction as a measurement value from the pressure sensor; and corrects the measured pressure and the change therein in consideration of the shape of the pipette tip, the predetermined suctioning rate, and the period of suction time. As a result, a normal suction of a specified liquid quantity, a suction deficiency, or an empty state can be identified, and the state of the suction of the specified liquid quantity during dispensing can be accurately ascertained.

In the second means for solving the problems according to the above liquid suction monitoring dispensing apparatus, the measured pressure change is compared with a preset threshold value, and based on a pressure value that deviates from the threshold value, time-series changes of the suction state can be found at a high level of accuracy. As a result, based on the obtained time-series changes of the suction state, a normal suction of a specified liquid quantity, and a suction deficiency can be determined, and the suction state during dispensing can be accurately ascertained.

In the third means for solving the problems according to the above liquid suction monitoring dispensing apparatus, since the pipette tip having the small diameter section and the large diameter section is used, influence of the insertion into the liquid can be minimized and a minute quantity of liquid and also containers with various kinds of shapes can be handled.

BEST MODE FOR CARRYING OUT THE INVENTION

Hereinafter, an embodiment of the present invention is specifically described.

However, the present embodiment is to give a specific description with a purpose of providing better understanding of the intent of the present invention, and does not limit the content of the invention unless otherwise specified.

[Configuration]

As shown in FIG. 1, a pipetter 10 of the present embodiment is provided with: a pipette tip 3 which is supported substantially vertically immediately above an opening section 1$a$ of a container 1, and a distal end section (bottom end section) 3$a$ of which is to be inserted into liquid accommodated in the container 1; a nozzle member 4 that is fitted on a top end section 3$b$ of this pipette tip 3; a cylindrical suctioning/discharging mechanism 5 directly connected to this nozzle member 4; and a pressure sensor 7 that is connected to a side wall of the nozzle member 4 via a pipe or air hose 6. The distal end section 3$a$ of the pipette tip 3 is provided on a small diameter section 3$c$ having a thickness which allows insertion into the container 1, and the top end section 3$b$ is provided on a large diameter section 3$d$ that continues from the small diameter section 3$c$ and that is connected to the suctioning/discharging mechanism 5 via the nozzle member 4. Moreover, the small diameter section 3$c$ and the large diameter section 3$d$ are connected to each other via a funnel-shaped transitional section 3$e$. Another possible shape of the transitional section 3$e$ may be a shape having steps or a conical shape with a tapered distal end.

A pressure measurement result from the pressure sensor 7 is transmitted to a control section 8, and based on the pressure measurement result, the control section 8 identifies and monitors: a liquid suction quantity and time-series changes thereof; and a specified normal liquid suction quantity, a suction deficiency, or a suction state such as an empty state, and controls the operation of the suctioning/discharging mechanism 5 according to the suction state.

In addition to liquid quantity detection, the control section 8 operates a lifting and lowering mechanism not shown in the drawing (in the arrow direction A) to shift the pipetter 10 in a perpendicular direction and bring the distal end section 3$a$ of the pipette tip 3 into and out of liquid 2 accommodated within the container 1. Also when inserting, the distal end section 3$a$ of the pipette tip 3 is inserted into a position in close proximity to the bottom section of the container 1 to allow liquid suction, and the suctioning/discharging mechanism 5 is operated (in the arrow direction B) to bring air into and out of the pipette tip 3, thereby performing control of suction or discharge of the liquid 2.

In this control section 8, when detecting dispensed quantity, the distal end section 3$a$ of the pipette tip 3 is lowered, and the lowering is stopped and a suction position is decided when the distal end section 3$a$ has reached a position (hereinafter, referred to as a deepest zone) a certain distance (for example, 1 mm) above the bottom of the container 1. Then the suctioning/discharging mechanism 5 is operated and suction at a certain suction quantity is performed to suction the liquid inside the container 1, and the state of suction including: whether or not a normal specified quantity of liquid is being suctioned; whether or not there is a suction deficiency or an empty state; whether or not the suction quantity has not reached the predetermined quantity due to clogging in the distal end section 3$a$ of the pipette tip 3; or whether or not a period of time for suction has normally elapsed, is monitored, while continuing the suction. In the case where the predetermined period of suction time has elapsed without any abnormality, it is judged that a specified quantity of liquid suction has been normally performed, and the operation of the suctioning/discharging mechanism 5 is terminated to stop suction.

The control section 8 determines the result measured by the pressure sensor 7 as described below.

(1) Liquid Surface Determination

In the case where the suctioning/discharging mechanism 5 is operated while the pipetter 10 is being lowered and the pressure at the pipette tip 3 has been made negative, then as shown in FIG. 2, if the pressure rapidly reduces after it rises from atmospheric pressure for a short period of time, and the pressure is reduced above a set value, then it is determined that the distal end section 3$a$ of the pipette tip 3 has reached the surface of the liquid.

As an example of this case, the pressure set value is set to −0.12 atm (gauge pressure; the same in the following).

(2) Empty Determination

In the case where the distal end section 3a of the pipette tip 3 is positioned in the deepest zone of the container 1, if the pressure does not reduce below a set value, it is determined that the inside the container is empty.

As an example of this case, the pressure set value is set to −0.2 atm.

(3) Clogging Determination

In the case where the distal end section 3a of the pipette tip 3 is positioned in the deepest zone of the container 1, if the pressure reduces rapidly and exceeds a set value, it is determined that clogging has occurred.

As an example of this case, the pressure set value is set to −2 atm.

(4) Deficiency Determination

In the case where the distal end section 3a of the pipette tip 3 is positioned in the deepest zone of the container 1, when the liquid is depleted during the suction, air is suctioned and the value of the pressure sensor slightly reduces. Therefore when the pressure reduces during the suction, this pressure is reduced for a set pressure, and in the case where this continues for a certain period of time, the liquid quantity is deficient.

As an example of this case, the reduction pressure is set to −0.4 atm and the continued time is set to 100 msec.

(5) Time-Out

In the case where the distal end section 3a of the pipette tip 3 is positioned in the deepest zone of the container 1, if the suction does not stop after the set period of time has elapsed, all processes are terminated and the operation returns to the standby state.

As an example of this case, the time-out time is set to: $T_O = A + \alpha$, where the elapsed time $\alpha = 80$ msec of 1 sampling cycle is added as the elapsed time to the time A for suctioning the predetermined volume of the liquid.

[Dispensing Method]

1. In the Case of Appropriate Dispensing

As shown in FIG. 3, first, the suctioning/discharging mechanism 5 and the lifting and lowering mechanism are returned to their original positions, and the container 1 that accommodates the liquid to be dispensed is installed in a prescribed position of the dispensing apparatus to complete the preparation state of the dispensing apparatus (step 11).

The control section 8 initializes a data processing section having a built-in CPU, and takes in data transmitted from the pressure sensor 7 as digital data at a sampling rate of 80 times per 1 msec (millisecond) to enable an analysis of the pressure measurement result (step 12).

Subsequently, the lifting and lowering mechanism is operated towards the descending side to lower the pipette tip 3 for a predetermined distance, and the distal end section 3a of the pipette tip 3 is lowered so that it stops in the deepest zone (approximately 1 mm above the bottom) of the container 1 that accommodates the liquid. Then the suctioning/discharging mechanism 5 is operated towards the suction side to have the pipette tip 3 suction the liquid inside the container 1 (step 13).

Once the liquid suction is commenced, the pressure during the suction is measured by the pressure sensor 7, and the result of the measurement is sequentially transmitted from the pressure sensor 7 to the control section 8.

In the control section 8, this transmitted pressure information is A/D-converted and taken in as digital data at a predetermined sampling rate, and is subjected to data analysis to analyze the suction status for monitoring the states of the respective sections (step 14).

The control section 8 analyzes the data that is taken in at a prescribed sampling rate, and monitors that: the suction is discontinued after the set period of suction time that is set based on the specified liquid quantity has elapsed (step 15); no empty suction is performed (step 16); no clogging is occurring (step 17); and the liquid is being suctioned as prescribed and the liquid quantity is sufficient without any deficiency (step 18), and checks whether or not the set period of suction time has elapsed (step 19). If the prescribed suction time that is set based on the specified liquid quantity has not elapsed yet, then the operation returns to step 15 and continues to monitor the suction and the state thereof, and if the above prescribed suction time has elapsed, then the suction process normally completes (step 20).

When monitoring the suction state; in the case where the suction is continued even after the set suction time has elapsed (step 15), in the case where an empty suction is being performed (step 16), in the case where there is a clogging (step 17), or in the case where there is a deficiency in the liquid quantity (step 18), the suction is halted (step 21), error processing is performed (step 22), and the operation is terminated in a state where the suction process for this container 1 is halted.

If the suction is normally performed and the suction for the above prescribed suction time has been completed with acquisition of the prescribed suction quantity, which is a specified liquid quantity, then the suctioning/discharging mechanism 5 is stopped to keep the suction pressure constant, and data sampling is stopped and the lifting and lowering mechanism is operated towards the ascending side to raise the distal end of the pipette tip 3 until the distal end has come out from the top section of the container 1.

Having taken out the pipette tip 3 from the container 1, the pipetter 10 is shifted to a position of an examination container not shown in the drawing that is arranged so as to receive the suctioned liquid, and the lifting and lowering mechanism is operated to the descending side to lower the pipette tip 3 to a position where it enters the opening of the examination container, and then the suctioning/discharging mechanism 5 is operated to the discharging side so as to discharge the liquid inside the pipette tip 3 into the examination container.

Having discharged the liquid, the lifting and lowering mechanism is operated to the ascending side so as to shift the pipette tip 3 to above the examination container, and then the pipetter 10 is returned to the position in which the container 1 is arranged, and the dispensing operation is repeated.

2. In the Case of Inappropriate Dispensing

In the case where dispensing is not appropriate, the dispensing operation is processed as described below.

(In the case of empty suction/liquid surface detection)

As shown in FIG. 4, the control section 8 takes in atmospheric pressure as data from the pressure sensor 7 before suction is commenced (step 21), and the suctioning/discharging mechanism 5 is operated to the suction side to measure the suction pressure (step 22), and the nozzle member 4, and therefore the pipette tip 3 is lowered for a predetermined amount distance (step 23).

To continuously perform liquid suction, in the case where the liquid is being normally suctioned, the following empty suction processing step and liquid surface detection processing step (step 25, step 27) are skipped, and the operation proceeds to the suction continuation processing step (step 26).

When the liquid is not being suctioned, a temporary pressure change at the point of contacting the liquid surface is monitored to detect whether or not the liquid has been suctioned, while the pipette tip 3 is lowered (step 25). At this time, if there is a set pressure change, it is determined that the liquid surface has been detected. If the liquid surface has been detected, the operation proceeds to the suction continuation processing step (step 26).

If there is no pressure change of the liquid surface detection, the pressure change monitoring is continued, and changes in both of the lowering amount and the measurement pressure of the pipette tip 3 are analyzed to determine whether or not an empty suction is being performed (step 27).

In this determination, if suction is performed in the empty container 1, then the suction pressure required for the liquid suction is not achieved, time passes while there is a substantially constant pressure with almost no change in the pressure, and a suction curve line in the case of a normal suction is not shown. Therefore if the pressure does not reduce below the set pressure even after the prescribed suction time has elapsed, it is determined that there is empty suction (refer to FIG. 2). If the period of time that has elapsed is short and it cannot be determined as an empty suction, the operation returns to the step 24 and repeats the detections of empty suction and liquid surface.

In the case where the liquid suction and the liquid surface have been detected and the liquid suction is further continued (step 24, step 25), the operation proceeds to the suction continuation processing step (step 26).

In the case where there is no liquid surface detection or there is an empty suction, the suction is immediately stopped (step 28).

If there is an empty suction, the examination sample relevant to the empty container 1 used in the suction is removed after dispensing.

(In the Case of Clogging)

As shown in FIG. 5: suction is commenced; the control section 8 performs sampling of data from the pressure sensor 7 (step 31); a suction flow rate and a suction quantity is calculated based on the pressure and the elapsed time (step 32); and the relationship between the suction quantity and the pressure is analyzed (step 33).

In the case where clogging has occurred: the pressure gradient becomes steeper compared to the case of a normal suction; the initial rising in the suction curve line is sharp; the degree of change becomes sharper over time; and a reduction in the pressure per unit time becomes more significant, and these suggest that the pattern of change in pressure clearly differs from that where there is a trend for a pressure reduction change in a direction in which the pressure reduction gradually becomes smaller in the case of a normal suction (refer to FIG. 2). Therefore, whether or not the pressure changes in a direction in which the pressure reduction rapidly changes and whether or not the pressure change has exceeded the pressure set value (−2 atm) are inspected and identified (step 34).

As a result of this analysis, in the case where there is no clogging, the suction is continued, and the suction is completed when the suction of a prescribed quantity, which is a specified liquid quantity, has been performed (step 35). Moreover, in the case where clogging has been identified, it is treated as a suction quantity deficiency and the suction is halted (step 36).

In this case, the examination sample relevant to the container 1 in which clogging has occurred is removed after dispensing.

As a measurement example of clogging, an example of suctioning 500 µl of grease instead of the above mentioned liquid is shown in FIG. 7. As shown in this graph, the grease suction causes a reduction in the pressure from atmospheric pressure to approximately −2 atm per approximately 10 msec, creating a clogging state. That is to say, the pressure change rate is approximately −0.2 atm/msec. When clogging occurs, suction becomes impossible, and this pressure value stays the same until the suction time is completed.

According to this result, the pressure change in the initial state caused by clogging shows a rapid reduction in pressure until the suction becomes impossible. Therefore if a threshold value is set in a timing of rapid initial pressure reduction or if a threshold value is set for the change rate, to detect clogging, then unnecessary suction processing from that point can be avoided.

(In the Case of Liquid Quantity Deficiency)

As shown in FIG. 6, when suction is commenced, the control section 8 samples data from the pressure sensor 7 (step 41), and monitors changes in the pressure over time (step 42).

As a result of pressure change monitoring: whether or not the pressure rapidly falls and the pressure reduction within the set range is continued for a set period of time (step 43); whether or not the pressure then rapidly rises and the pressure rises within the set range is continued for a set period of time (step 44); and whether or not an empty suction has started after these rapid changes in the pressure (step 45), are inspected in this order. If there is an empty suction, then it is determined that there is a liquid quantity deficiency and the suction is immediately stopped (step 46) while performing error processing (step 47), and the processing step of monitoring this liquid quantity deficiency is completed.

When monitoring the pressure change, if the pressure to be monitored rapidly falls and then there is neither a rapid increase in the pressure nor empty suction, then it is considered that these events are caused by reasons other than a liquid quantity deficiency. Accordingly, the operation returns to step 43, and new data is taken in again to re-perform pressure change monitoring.

The examination sample relevant to the container 1 in which a liquid quantity deficiency has occurred is removed after dispensing.

As an example of a measurement of liquid quantity deficiency, FIG. 8 shows a result of dispensing operations in the cases where solutions (Lysis solution, DW solution) of two types having different viscosities are used and suctions of three specified liquid quantities (100 µl, 200 µl, 400 µl) are performed and (1) the liquid inside the container is not deficient, (2) the quantity of the liquid inside the container is equivalent to the suction quantity, and (3) the liquid inside the container is 50 µl short.

According to this result, the suction of Lysis solution with a higher level of viscosity requires greater suction pressure. However, both of Lysis solution and DW solution show changes that follow the suction curve line without having clogging, except for the case of having a liquid quantity deficiency.

Moreover, in the case of liquid quantity deficiency; the suction pressure rapidly reduces due to a reduction in water head pressure immediately before the liquid depletes; the measurement pressure rapidly reduces; when the liquid has depleted, air is suctioned, resulting in a rise in the pressure; and the pressure rises until it has reached the pressure required for keeping the suctioned liquid within the pipette tip 3 and then reaches an equilibrium state.

As described above, if the liquid quantity is deficient, a rapid pressure reduction in a short period of time followed by a rapid pressure rise occurs at the end of the suction curve line, and changes that are different from that in the case of the suction curve line in a normal dispensing with no liquid quantity deficiency are shown. According to these clearly different changes, the case of having liquid quantity deficiency can be clearly differentiated from the case of a normal dispensing.

Therefore if a standard suction curve line that corresponds to the pipette tip 3 has been pre-obtained, even in the case where the liquid quantity is 50 μl short, a liquid deficiency can be detected by evaluating the point in which the above suction curve line differs from this standard suction curve line from a comparison between them.

Furthermore, it can be seen that the pressure change wave forms shown in FIG. 8 are clearly divided into three regions (I, II, III). The first region I corresponds to the small diameter section 3c of the pipette tip 3, the second region II corresponds to the transitional section, and the third region III corresponds to the large diameter section 3d. As seen in FIG. 8, the changes in the pressure are dependent on the shape of a pipette tip.

[Dispensing Apparatus]

FIG. 9 is a perspective view showing an entire liquid suction monitoring dispensing apparatus 50 according to the present embodiment. The liquid suction monitoring dispensing apparatus 50 has a base plate 51 on the bottom side thereof, and on the base plate 51 there is attached an LM guide 52 along the X axis direction (within the horizontal plane), and there is provided a stage 53 so as to be able to move in the X axis direction, being guided by the LM guide 52. On the base plate 51 there is provided a main body portion 54 which is provided so as not to be able to move within the horizontal plane which includes the X axis direction.

The main body portion 54 is provided with a nozzle head 61 in which there are provided a series of six of the nozzle members 4 to which the pipette tips 3 are attached, and the cylindrical suctioning/discharging mechanism 5. Moreover, there is provided a prismatic-shaped remover 58 for attaching and removing the pipette tips 3 attached to the nozzle members 4, and the remover 58 is able to move in the vertical direction with respect to the nozzle head 61, and in the positions that correspond to the respective nozzle members 4, there are provided six drilled through holes having inner diameters that are slightly greater than the outer diameter of the nozzle member 4 and are slightly smaller than the outer diameter of the pipette tip 3.

The stage 53 is able to move in the X axis direction so as to go under the main body portion 54. On the stage 53 there are provided: tube holes 55a that load or accommodate containers such as sample tubes in positions that correspond to the positions of the series of six of the nozzle members 4; tip holes 55b that load or accommodate the pipette tips 3 in positions that correspond to the above mentioned positions; and cartridge racks 56 that load or accommodate cartridge containers in positions that correspond to the above mentioned positions.

In order to attach the pipette tip 3 to the nozzle member 4, the nozzle head 61 is lowered so as to insert the nozzle member 4, from above, into the pipette tip 3 accommodated in the tip hole 55b of the stage 53.

Inside the nozzle head 61 there are provided six pressure sensor units (not shown in FIG. 9) having built-in pressure sensors 7 that link to the nozzle members 4 via thin pipes, so as to correspond to each of the nozzle members 4. On the upper side of the nozzle head 61 there are provided plungers 57 that slide within the cylinders of the suctioning/discharging mechanism 5, and the plungers 57 are driven by a P axis motor 59 fixedly provided on the nozzle head 61. The nozzle head 61, the plungers 57, and the P axis motor 59 are driven in the vertical direction by a Z axis motor 60 provided on the base plate 51. Thereby, the distal end of the pipette tip 3 attached to the nozzle member 4 can be lowered to the deepest zone of the container.

Moreover, on the lower side of the nozzle member 4 there are provided a magnet unit 62 and a magnet motor 63. The magnet unit 62 is driven so as to come into close proximity to and move away from the axis of the nozzle member 4. The magnet unit 62 is not moved in the vertical direction by the Z axis motor 60, and is fixed in the vertical direction with respect to the base plate 51.

The stage 53 and the main body portion 54 need to be relatively moveable, and the main body portion 54 may be made moveable with respect to the stage 53 within the horizontal plane. Furthermore, the number of the nozzle members 4 is not limited to six.

Effects

In the dispensing method according to the present embodiment, without detecting the surface of liquid accommodated within a container, the quantity of the suctioned liquid can be found by only measuring a pressure change. Moreover, liquid surface detection can also be performed based on the result of pressure measurement. A suction state having abnormalities such as emptiness, clogging, and volume deficiency can be easily identified by comparing these abnormal states with the normal suction state, and the dispensing state of a specified liquid quantity can be ascertained based on an analysis of pressure changes with respect to the suction state of the liquid.

Furthermore, by making a comparison with a preset threshold value, whether the suctioned liquid quantity is deficient or sufficient, and also whether the liquid inside the container has depleted and the container has become empty can be detected.

Moreover, by having the distal end of the pipette tip positioned with a certain gap from the bottom of the container, the suction state becomes uniform, the reliability of a measurement of a specified liquid quantity is improved, and a dispensed quantity can be detected at a high level of accuracy.

In the dispensing apparatus of the present embodiment, the control section operates the lifting and lowering mechanism to insert the distal end of a pipette tip into a deepest zone of a container that accommodates liquid to be measured, operates the suctioning/discharging mechanism to suction the liquid into the pipette tip, and receives input of the pressure inside the pipette tip during the suction from the pressure sensor. Then based on the measured pressure, changes therein, and a preset threshold value, a pressure value that deviates from the threshold value is corrected in consideration of the shape of the pipette tip, the predetermined suctioning rate, and a period of time for the suction. As a result, a liquid quantity of the suction, and a time-series change thereof, can be found at a high level of accuracy.

Accordingly, based on the obtained liquid suction quantity and the time-series change, a normal suction of a specified liquid quantity, a suction deficiency, or an empty state can be identified. As a result, the suction state during dispensing can be accurately ascertained.

BRIEF DESCRIPTION OF THE REFERENCE SYMBOLS

Figure 1:
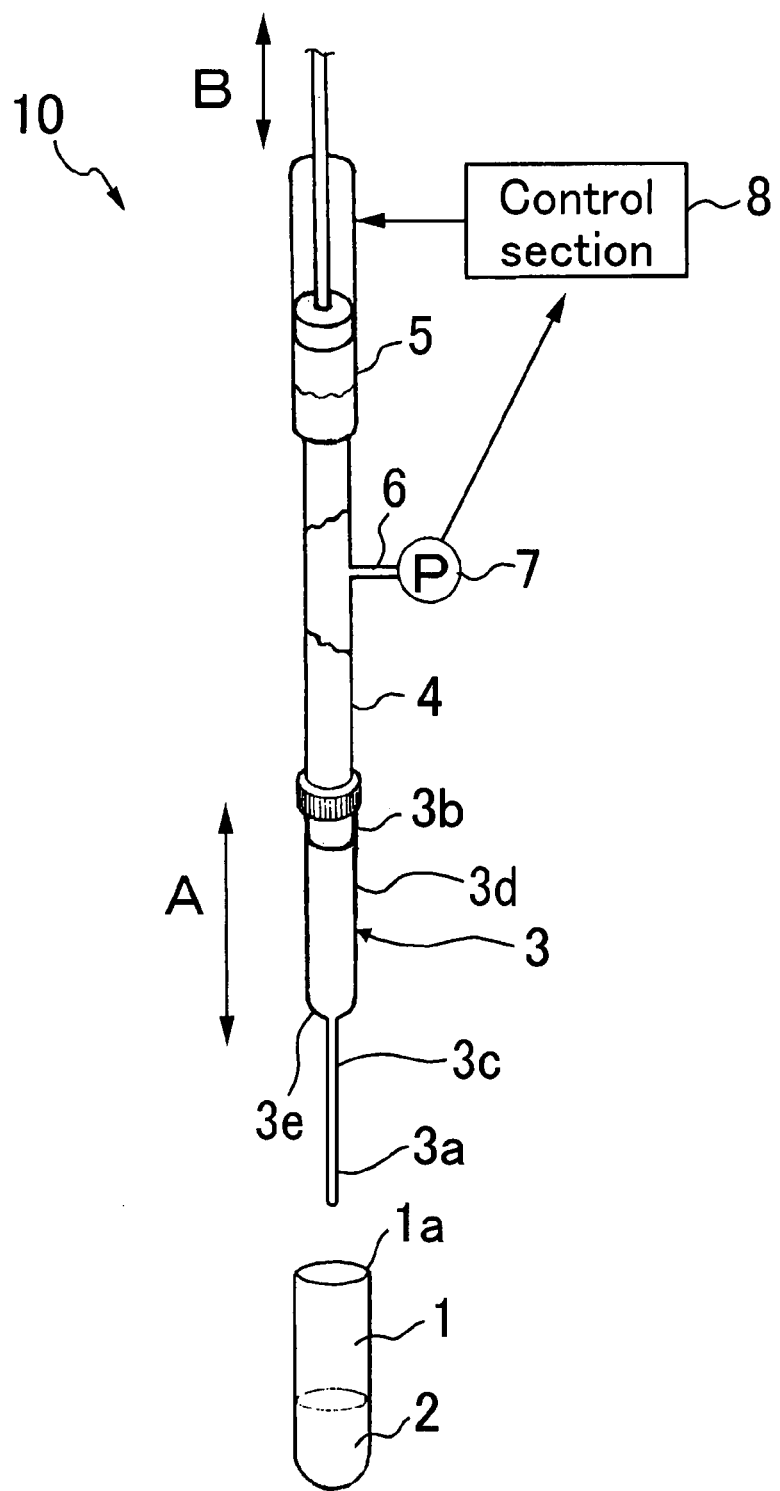
FIG. 1 is a partial perspective explanatory drawing showing a pipetter according to an embodiment of the present invention.
Figure 2:
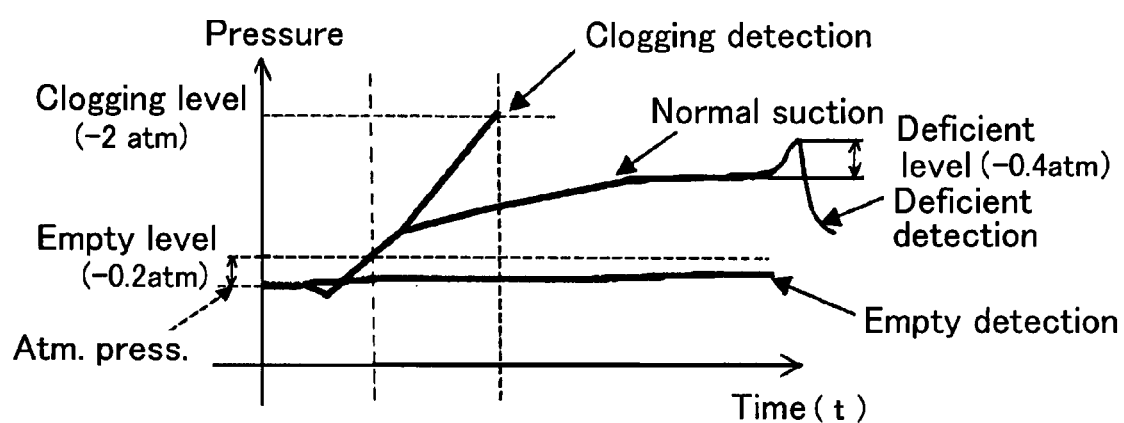
FIG. 2 is a graph showing a result of pressure measurements in a suction operation according to the embodiment of the present invention.
Figure 3:
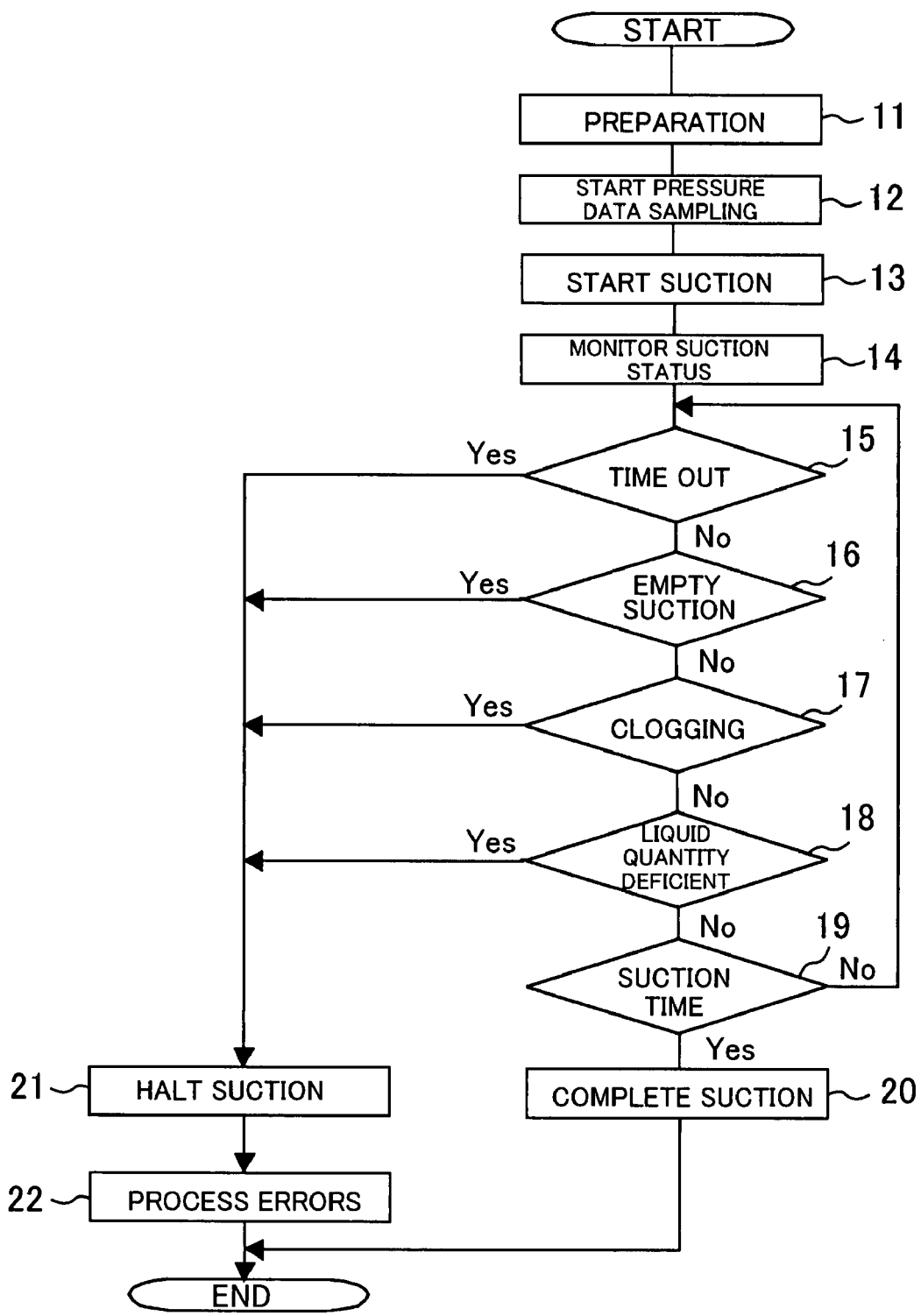
FIG. 3 is a flow chart of a suction operation that uses the pipetter according to the embodiment of the present invention.
Figure 4:
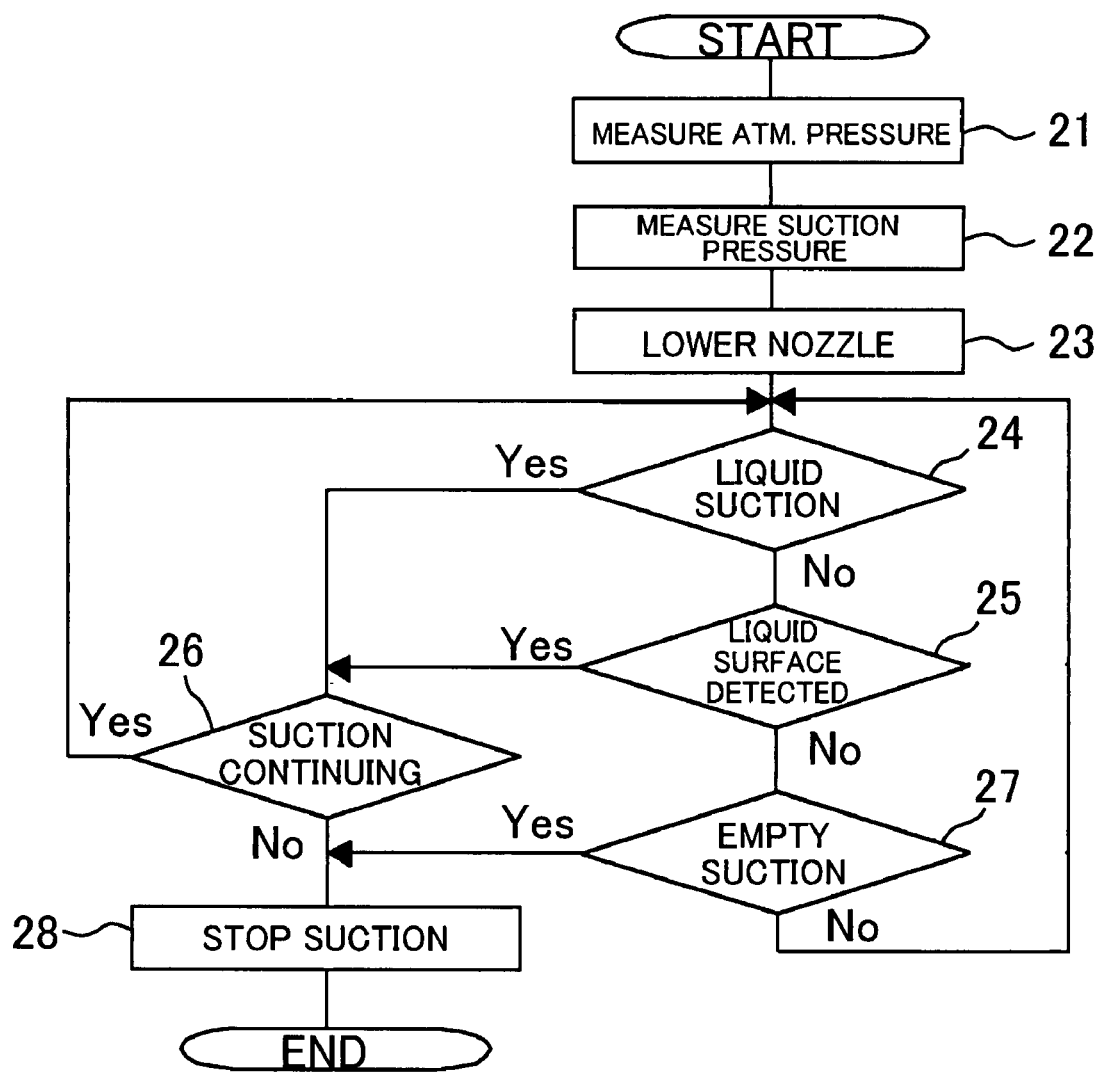
FIG. 4 is a flow chart of liquid surface detection and empty suction monitoring with use of the above mentioned pipetter.
Figure 5:
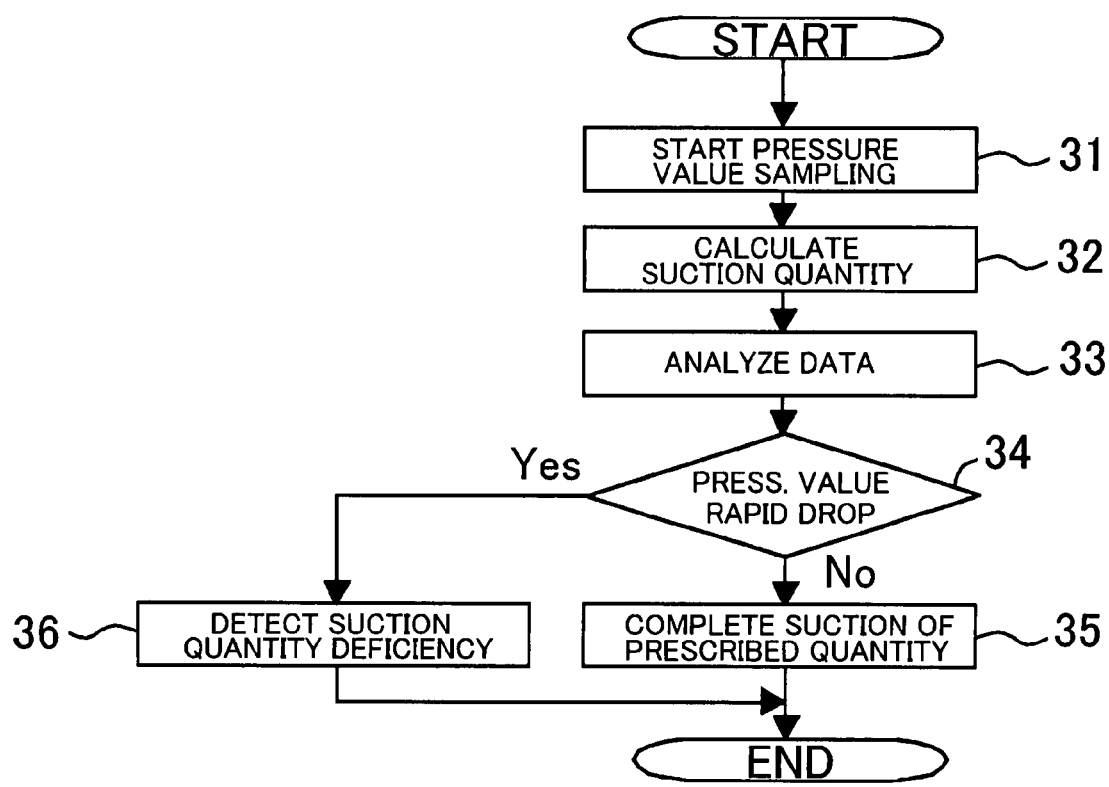
FIG. 5 is a flow chart of clogging monitoring with use of the above mentioned pipetter.
Figure 6:
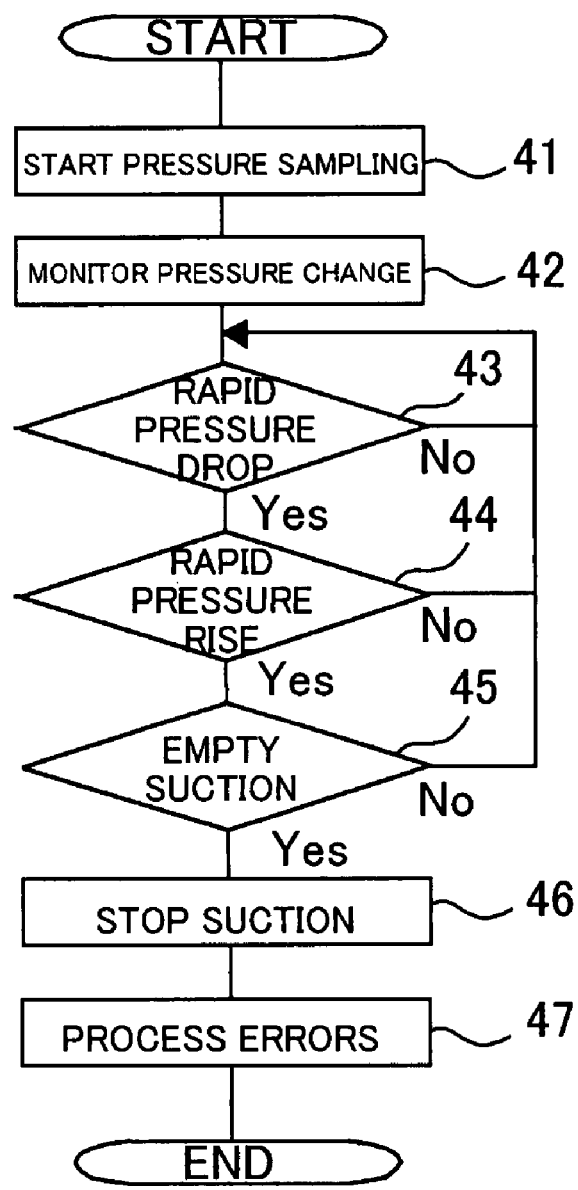
FIG. 6 is a flow chart of monitoring deficient liquid quantity with use of the above mentioned pipetter.
Figure 7:
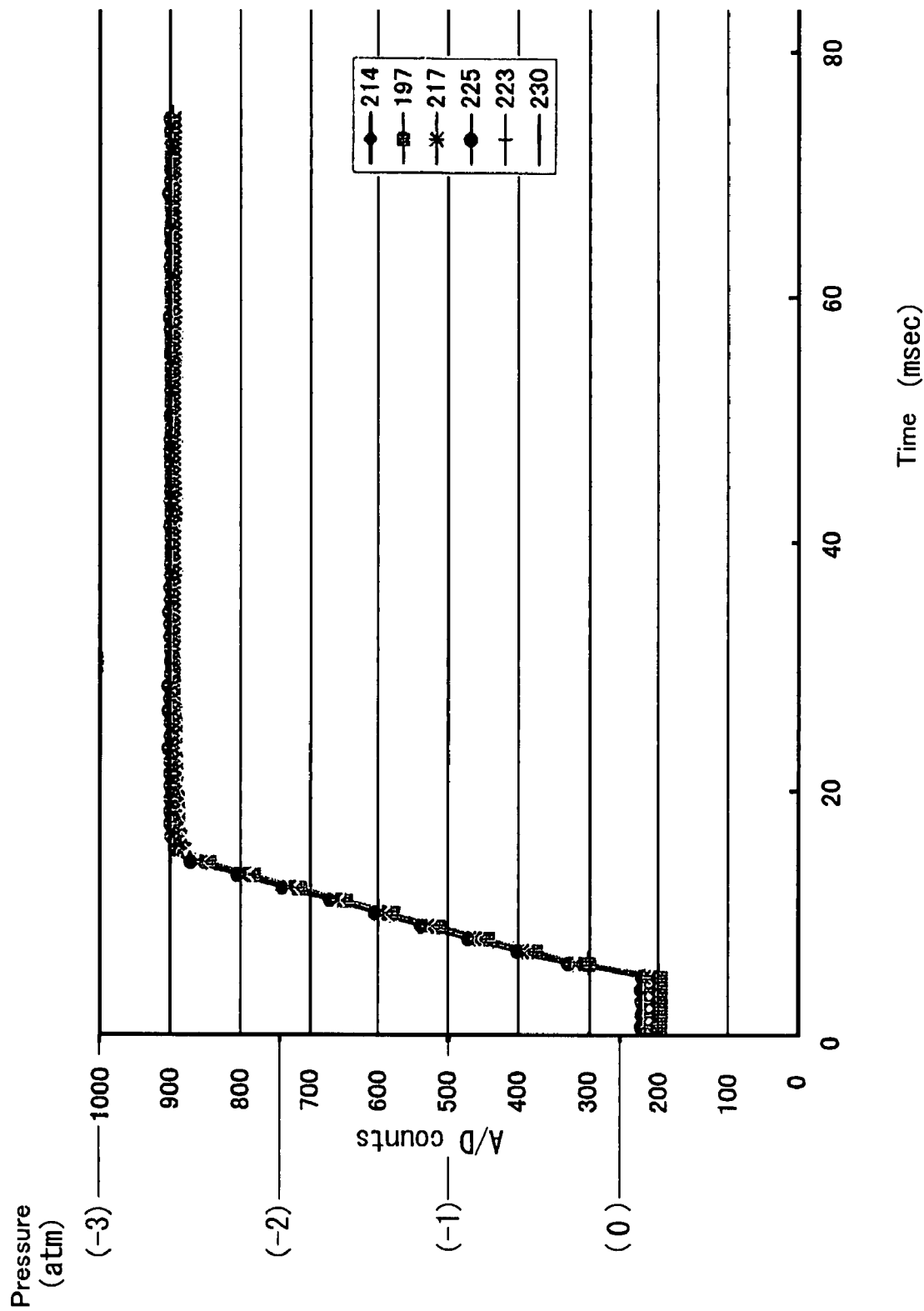
FIG. 7 is a graph showing a result of measurements in a clogging state in the suction operation according to the present invention.
Figure 8:
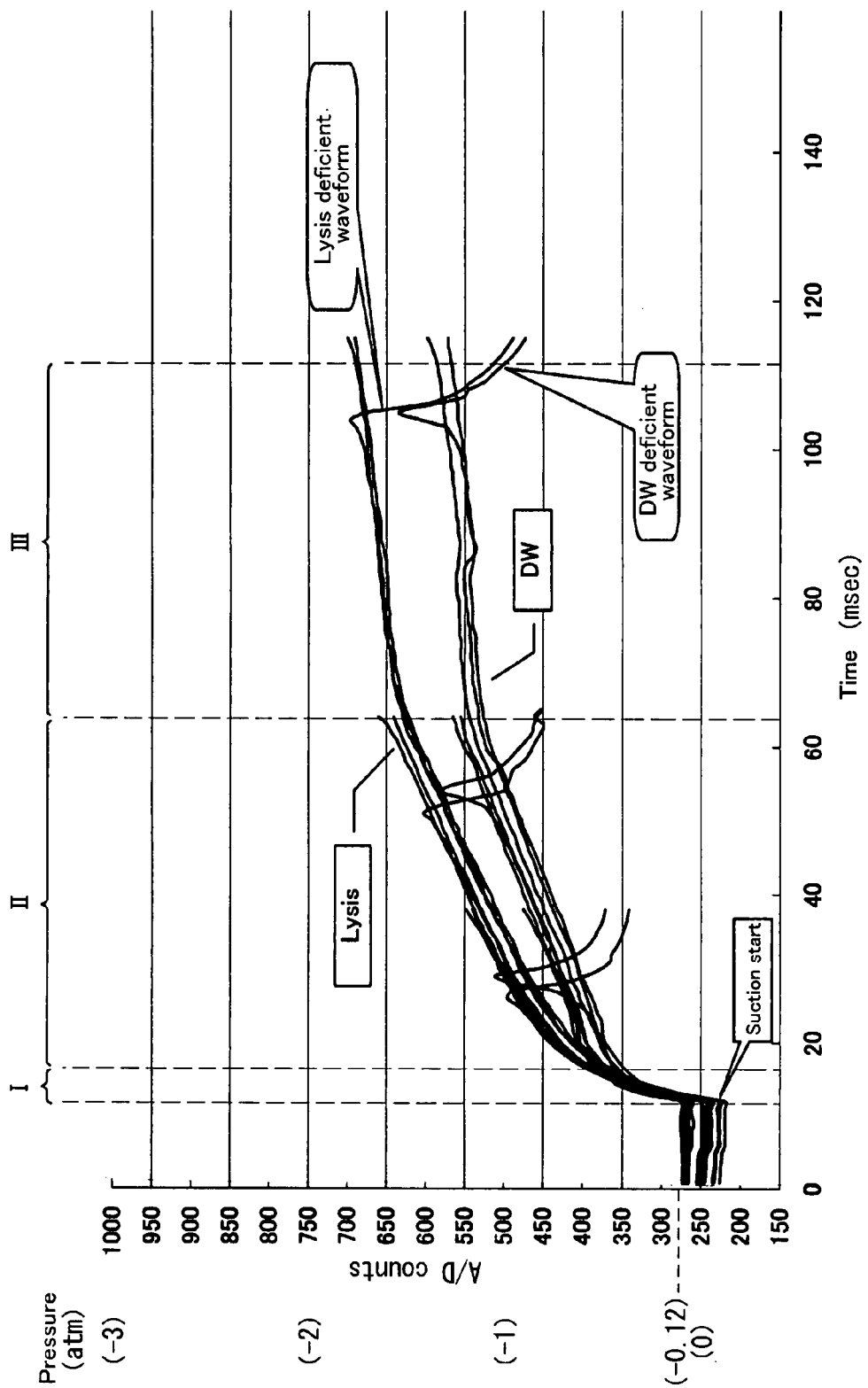
FIG. 8 is a graph showing a result of measurements in a liquid quantity deficient state in the suction operation according to the present invention.
Figure 9:
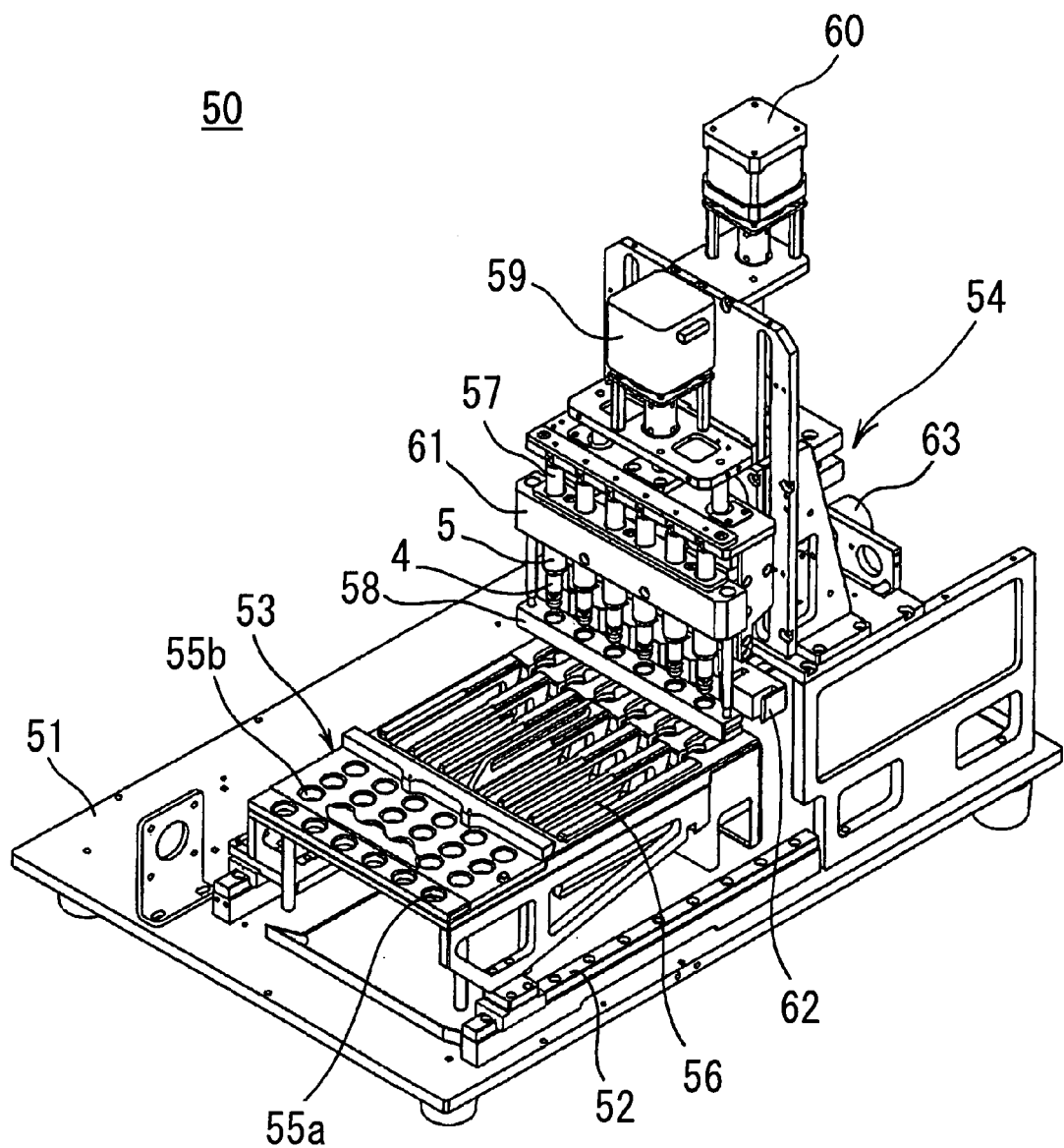
FIG. 9 is an overall perspective view of a liquid suction monitoring dispensing apparatus according to the embodiment of the present invention.

1 Container
2 Liquid
3 Pipette tip
3a Distal end section
3b Top end section
4 Nozzle member
5 Suctioning/discharging mechanism
6 Pipe
7 Pressure sensor
8 Control section
10 Pipetter
50 Liquid suction monitoring dispensing apparatus

The invention claimed is:

1. A method of detecting dispensed quantity for detecting a liquid quantity of liquid suctioned and discharged by a dispensing apparatus having: a pipette tip; a liquid suctioning/discharging mechanism for said pipette tip; a pressure sensor that detects a pressure inside said pipette tip; and a lifting and lowering mechanism for said pipette tip, wherein said method comprises:
an insertion step for inserting a distal end of said pipette tip into a deepest zone of a container that accommodates liquid to be measured, the deepest zone being at a position that is distanced upward from a bottom of said container by a predetermined distance that is greater than zero;
a suctioning step for suctioning, using the liquid suctioning/discharging mechanism, said liquid into said pipette tip at a predetermined suctioning rate without moving said pipette tip from the deepest zone;
a suction pressure measuring step for measuring a pressure change during suctioning said liquid into said pipette tip at the predetermined suctioning rate without moving said pipette tip from the deepest zone; and
a suction detecting step for detecting a suction state based on a measured pressure change, a shape of said pipette tip, said predetermined suctioning rate, and a period of suction time, wherein the liquid quantity is detected based on the suction state.

2. A method of detecting dispensed quantity according to claim 1, wherein said suction detecting step compares said measured pressure change with a preset threshold value, and detects the suction state based on a pressure value that deviates from said threshold value.

3. A method of detecting dispensed quantity according to claim 1, wherein said suction detecting step compares said measured pressure change with a preset threshold value, and wherein in said suction detecting step, the presence or absence of a suction deficiency, or an empty suction is detected based on a pressure value that deviates from said threshold value.

4. A method of detecting dispensed quantity according to claim 1, wherein in said suction detecting step, the presence or absence of said pipette tip is detected based on the presence or absence of said measured pressure change.

5. A method of detecting dispensed quantity according to claim 1, wherein in said suction detecting step, an occurrence of clogging is detected if a change rate of said pressure change exceeds a preset value.

6. A method of detecting dispensed quantity according to claim 1, wherein said pipette tip has a small diameter section on which said distal end is provided, and a large diameter section that continues from said small diameter section and that can be connected to said suctioning/discharging mechanism, and in said insertion step, said small diameter section is inserted into said liquid.

7. A liquid suction monitoring dispensing apparatus comprising:
a pipette tip;
a lifting and lowering mechanism for said pipette tip;
a liquid suctioning/discharging mechanism for said pipette tip;
a pressure sensor that detects a pressure inside said pipette tip; and
a control section that: operates said lifting and lowering mechanism so as to insert a distal end of said pipette tip into a deepest zone of a container that accommodates liquid to be measured, the deepest zone being at a position that is distanced upward from a bottom of said container by a predetermined distance that is greater than zero; operates said suctioning/discharging mechanism so as to suction said liquid into said pipette tip at a predetermined suctioning rate without moving said pipette tip from the deepest zone; receives input of a measurement value from said pressure sensor during suctioning said liquid without moving said pipette tip from the deepest zone; detects a suction state based on a measured pressure change, a shape of said pipette tip, said predetermined suctioning rate, and a period of suction time; and detects a liquid quantity of the liquid based on the suction state.

8. A liquid suction monitoring dispensing apparatus according to claim 7, wherein said control section compares said measured pressure change with a preset threshold value, and detects the suction state based on a pressure value that deviates from said threshold value.

9. A liquid suction monitoring dispensing apparatus according to claim 7, wherein said pipette tip has a small diameter section on which said distal end is provided, and a large diameter section that continues from said small diameter section and that can be connected to said suctioning/discharging mechanism.

10. A method of detecting dispensed quantity according to claim 2, wherein in said suction detecting step, the presence or absence of a suction deficiency, or an empty suction is detected based on a pressure value that deviates from said threshold value.

11. A method of detecting dispensed quantity according to claim 2, wherein in said suction detecting step, the presence or absence of said pipette tip is detected based on the presence or absence of said measured pressure change.

12. A method of detecting dispensed quantity according to claim 2, wherein in said suction detecting step, an occurrence of clogging is detected if a change rate of said pressure change exceeds a preset value.

13. A method of detecting dispensed quantity according to claim 1, wherein the suction detecting step for detecting a suction state comprises detecting at least whether or not a normal specified quantity of liquid has been suctioned, whether or not there is a suction deficiency, whether or not there is a liquid quantity deficiency, or whether or not the suction quantity has not reached a predetermined quantity due to clogging in the distal end section of the pipette tip;
- wherein at the suction detecting step, in the case where the period of suction time has elapsed without any abnormality, it is detected that the normal specified quantity of liquid has been suctioned and the operation of the liquid suctioning/discharging mechanism is terminated to stop suctioning said liquid into said pipette tip;
- wherein at the suction detecting step, in the case where it has been detected that the suction quantity has not reached the predetermined quantity due to clogging in the distal end of the pipette tip, suctioning said liquid into said pipette tip can be halted;
- wherein the clogging is detected when the measured pressure change becomes steeper compared to the case of a normal suction; and
- wherein the liquid quantity deficiency is detected when the pressure rapidly falls and the pressure reduction within a set range is continued for a set period of time, the pressure then rapidly rises and the pressure rise within a set range is continued for a set period of time, and an empty suction starts after the pressure rise.

14. A liquid suction monitoring dispensing apparatus according to claim 7, wherein the control section detects the suction state by detecting at least whether or not a normal specified quantity of liquid has been suctioned, whether or not there is a suction deficiency, whether or not there is a liquid quantity deficiency, or whether or not the suction quantity has not reached a predetermined quantity due to clogging in the distal end section of the pipette tip;
- wherein, in the case where the period of suction time has elapsed without any abnormality, it is detected that the normal specified quantity of liquid has been suctioned and the operation of the liquid suctioning/discharging mechanism is terminated to stop suctioning said liquid into said pipette tip;
- wherein, in the case where it is detected that the suction quantity has not reached the predetermined quantity due to clogging in the distal end of the pipette tip, suctioning said liquid into said pipette tip can be halted;
- wherein the clogging is detected when the measured pressure change becomes steeper compared to the case of a normal suction; and
- wherein the liquid quantity deficiency is detected when the pressure rapidly falls and the pressure reduction within a set range is continued for a set period of time, the pressure then rapidly rises and the pressure rise within a set range is continued for a set period of time, and an empty suction starts after the pressure rise.

* * * * *